United States Patent [19]
Radcliffe et al.

[11] Patent Number: 6,010,910
[45] Date of Patent: *Jan. 4, 2000

[54] DEVICES AND KITS FOR TESTING SERUM AND THE LIKE

[75] Inventors: David Michael Radcliffe; Cheryl Mary Anne Head, both of Basingstoke, United Kingdom

[73] Assignee: Oxoid Limited, Basingstoke, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/869,527

[22] Filed: Jun. 6, 1997

[30] Foreign Application Priority Data

Jun. 7, 1996 [EP] European Pat. Off. ............... 96304309

[51] Int. Cl.[7] .................................................. G01N 33/48
[52] U.S. Cl. ................................ 436/63; 422/61; 422/58; 436/808; 436/810; 436/166
[58] Field of Search .................................. 422/56, 58, 61, 422/100, 102, 164, 166, 63; 436/902, 808, 908, 810

[56] References Cited

U.S. PATENT DOCUMENTS

| | | | |
|---|---|---|---|
| 3,770,383 | 11/1973 | Price . | |
| 4,981,653 | 1/1991 | Marino | 422/58 |
| 5,017,342 | 5/1991 | Haberzettl et al. | 422/102 |
| 5,039,487 | 8/1991 | Smith | 422/56 |
| 5,413,761 | 5/1995 | Dulaney | 422/58 |
| 5,620,658 | 4/1997 | Jaunakais | 422/58 |

FOREIGN PATENT DOCUMENTS

| | | |
|---|---|---|
| 0 056 563 | 7/1982 | European Pat. Off. . |
| 0 112 077 | 6/1984 | European Pat. Off. . |
| 0 165 001 | 12/1985 | European Pat. Off. . |
| 0 368 624 | 5/1990 | European Pat. Off. . |
| 0 391 109 | 10/1990 | European Pat. Off. . |
| WO 96/01273 | 1/1996 | WIPO . |

*Primary Examiner*—Lyle A. Alexander
*Attorney, Agent, or Firm*—Lee, Mann, Smith, McWilliams, Sweeney & Ohlson

[57] ABSTRACT

An assay device for testing for the presence of an analyte in a sample liquid supported on a test surface, the device comprising a test stick having a handle portion to be held by a person performing the test and a mixing portion to contact the sample liquid, the mixing portion bearing a dried, pre-dosed reagent for the test, the dried reagent being reconstituted by contact of the mixing portion of the test stick with the sample liquid, and wherein the mixing portion is configured to provide a mixing surface to mix the reconstituted reagent with the sample liquid on the test surface.

9 Claims, 1 Drawing Sheet

DEVICES AND KITS FOR TESTING SERUM AND THE LIKE

FIELD OF THE INVENTION

This invention relates to devices and kits for testing sample liquids such as serum.

BACKGROUND OF THE INVENTION

Agglutination assays have been widely used for many years in the testing of sample liquids. Traditionally such testing was conducted on a solid surface such as a glass microscope slide, and the presence of an agglutinated particulate reagent observed either with the naked eye or with the aid of a microscope. Today, assay kits are commercially available in which the particulate reagent is provided in dry form pre-dosed onto an appropriate solid surface, for example a "test card". The sample liquid is applied to the card, for example, as a drop of serum. To conserve reagents and to facilitate handling of the test card without risk of contaminating the dried reagent, this reagent is usually located in a designated test area on the card, for example a clearly marked area of circular or other shape. It is usually necessary physically to agitate the sample liquid to encourage reconstitution of the dried particulate reagent. Thereafter the agglutination reaction can proceed and the test result can be evaluated by inspection of the test card after an appropriate time interval. Test devices of this type are taught, for example, in U.S. Pat. No. 3,770,383.

To reassure the user that the test card is performing satisfactorily it is desirable for a control to be provided. Typically this is a positive control which assists the user to appreciate the degree of agglutination (or its relative absence) indicative of a clearly positive test result. For example, in some assays this control is provided in the form of a liquid sample containing the analyte of interest, for example antibodies (e.g. in serum) raised against an infective agent of interest (such as *H. pylori* or Neisseria), or a preparation comprising antigens from the organism of interest (which may take the form of an antigen extract or a bacterial cell suspension). To maintain the integrity of this liquid control regent it must be stored at low temperature. The need for access to the refrigerated storage facilities severely limits the pratical situations under which such tests can be conducted.

Furthermore, in presently-available tests, reconstitution of the dried particulate reagent does not always occur effectively.

GENERAL DESCRIPTION OF THE INVENTION

In a first aspect the invention provides an assay device for testing for the presence of an analyte in a sample liquid supported on a test surface, the device comprising a test stick having a handle portion to be held by a person performing the test and a mixing portion to contact the sample liquid, the mixing portion bearing a dried, pre-dosed reagent for the test, the dried reagent being reconstituted by contact of the mixing portion of the test stick with the sample liquid, and wherein the mixing portion is configured to provide a mixing surface to mix the reconstituted reagent with the sample liquid on the test surface.

Preferably, the dried reagent is deposited as a plurality of closely-spaced spots. Preferably, the dried reagent is particulate and the test results are revealed by the occurrence of, or inhibition of, agglutination of the particles following mixing with the sample liquid.

The test surface may be any solid surface on which an assay, such as an agglutination assay, can be conducted and visualized. Conventionally, such surfaces take the form of test cards or similar. It is essential that under normal usage conditions applied sample liquid should remain essentially on the surface of the card. Accordingly, the test card should not soak up the sample liquid. Plastics material, in sheet or moulded form, is ideal, but absorbent materials such as paper and cardboard can easily be used if the working surface is rendered non-absorbent by pre-treatment or lamination with non-absorbent material, such as polypropylene or cellulose acetate. The presently available test card materials can be used with the assay device of the invention without any difficulty. The test surface does not constitute part of the present invention.

Where the test result is based on an agglutination assay the pre-dosed dried reagent on the test stick should be particulate. Conventional agglutination assay reagents are entirely suitable. Preferably, these are "latex", e.g. polystyrene, particles bearing a specific binding agent, such as an antibody or antigen, which leads to agglutination of the particles during the test. Typically these particles have a size in the range of 200 to 1000 nm, more usually 300 to 500 nm. The particles should have a colour that is distinctly visible against the test card background. Usually the particles themselves are strongly coloured, e.g. blue or red, and used against a white or other light-coloured card background. However, white particles can be used against a dark, e.g. black, background. Erythrocytes or Protein A-bearing particles are conventional alternatives to latex particles in some tests. In the presence of a "positive" sample, agglutination may either be caused or inhibited. For the purposes of the invention there is no necessity for the agglutination reagent to differ from those conventionally used.

In contrast to existing procedures, advantages are obtained if the sample liquid is not applied directly onto the pre-dosed dried reagent. We have noted that direct drop-wise addition of the sample liquid onto a pre-dosed reagent can create problems of poor or uneven release of the dried material, and "clumping" of the dried material which can be confused with true agglutination. In accordance with the invention it is preferable to add the sample liquid to the test card (which is not pre-dosed with the dried reagent). After addition, the sample liquid is moved and mixed with the pre-dosed reagent by use of the assay device of the present invention, ensuring uniform and effective reconstitution of the dried reagent before the agglutination reaction commences.

Conveniently the test stick comprises plastics, card or similar material of sufficient rigidity to facilitate mixing of the reagent and sample. In a preferred embodiment the test stick is provided as an essentially straight component (conveniently essentially planar, such as a spatula or the like), but wherein the mixing portion is joined to the handle portion by a region which is flexible (e.g. foldably deformable), such that the mixing portion can readily be bent out of the line of the stick to provide a mixing surface (angled relative to the handle portion of the stick) which facilitates ease of mixing of the reconstituted reagent and the sample liquid. This can readily be achieved by having a line of weakness, such as an impressed fold line or crease, perforation line, or a partial cut, running across the width of the stick close to one end. Simple finger pressure on the handle portion of the stick while the mixing portion is touching a surface, such as the test card, can cause the stick to flex at the line of weakness. The line of weakness in effect defines the boundary between the mixing portion and the handle portion.

Alternatively, the test stick may be formed of resiliently deformable material such that the stick can be bent during use to provide the mixing portion at an angle to the handle portion, thereby facilitating mixing of the sample with the test reagent.

Pre-dosing of the reagent can readily be achieved using conventional reagent deposition technology such as reagent printing and micro-pipetting. Typically the total volume of deposited reagent will be from about 1 to about 50 μl, which may be applied as more than one spot. Precise positioning can be achieved using a X-Y plotter, for example. After deposition, the reagents can be dried by using conventional procedures. The provision of stabilising agents such as nonspecific proteins, (e.g. BSA), and/or carbohydrates and sugars (such as sucrose, sorbitol or trehalose), is beneficial. A typical aqueous buffer may contain from about 1 to about 30 mg/ml BSA and from about 10 to about 100 mg/ml sucrose. These can be included in deposition buffers or added subsequently in accordance with conventional procedures. Typical buffers are phosphate buffer, usually at a pH of about 7, glycine buffer, Tris buffer and borate buffer.

The dry reagents of the invention can also incorporate additives that improve the performance of the assay, for example inhibitors for non-specific binding, e.g. a surfactant such as "Tween 20", and eliminators of interfering factors such as Rheumatoid-factor in serum. It will be appreciated that drying of reagents on the test stick increases the stability of the reagent (e.g. proteinaceous substances), especially at ambient temperatures.

It is preferred that at least the mixing portion (or the region thereof upon which the dried reagent is deposited), and desirably the whole test stick, is formed of a transparent or translucent material. This has the advantage that a person using the test stick in the course of an assay can readily determine visually when the dried reagent has been properly reconstituted and released from the test stick. A number of transparent or translucent plastics materials are known and which have properties suitable for making test sticks in accordance with the invention. These include polystyrene, polyethylene, polypropylene, polymers of acrylic or methacrylic acids, and related compounds and derivatives of the foregoing.

A further optional feature of the test stick is that it is configured so as to be capable of being used to collect bacterial colonies from the surface of agar plates. It is also a preferred feature that the test stick is capable of capturing a small volume of liquid (such as an aqueous sample liquid). Typically the liquid will be captured by a specially adapted region of the mixing portion, and desirably the liquid will be held separated from the dried reagent so as to prevent premature reconstitution thereof. Typically the liquid will be captured by surface tension and/or capillary action. For example, the liquid capture region may take the form of a small loop at one end region of the test stick (similar to those known for conventional inoculating loops), or may take the form of one or more narrow channels in the test stick, similar (for example) to the nibs of fountain pens.

The captured liquid may be deposited on the surface of a test card by touching the liquid capture region of the test stick onto the surface of the test card, so as to contact the captured liquid with the test card. Alternatively, the liquid capture region may be deformed by pressing against the test card, so as to release the captured liquid.

In certain embodiments it may be desirable to provide a plurality of substances on the test stick, each of the substances being formed as a discrete dried spot. For example, where substances are incompatible upon medium or long term storage together, they can be provided on the test stick as separate dried spots which only mix upon reconstitution during performance of the assay, such that they are sufficiently stable for the few minutes which it takes to perform and read a typical assay.

In a second aspect the invention provides a kit for testing for the presence of an analyte in a sample, the kit comprising the assay device defined above. More particularly, the kit will conveniently comprise a plurality of such assay devices. Preferably the plurality of test sticks will be provided as a "tear-off" array of separable, disposable sticks, preferably in a side-by-side arrangement, each stick being separated from adjacent sticks by a line of weakness (such as a fold, crease, partial cut line, perforation etc). In a preferred embodiment the dried test reagent comprises an antibody specific for a Lancefield group-specific antigen. Desirably, the kit will comprise a plurality of arrays of sticks, each array of sticks having an antibody specific for a different Lancefield group-specific antigen.

The kit will typically further comprise instructions for use. Other components may be included with advantage. Such optional components include a test card which provides a test surface to support the sample liquid during the assay. Preferably the test sticks and the test card (if provided) are disposable. Additionally, the Lancefield grouping agglutination assay, used to assign streptococci to one of the various Lancefield groups, requires an extraction step performed on the bacterial cells prior to the assay—in a kit for performing Lancefield grouping assays therefore, it is desirable to include reagents for performing the extraction (such as enzyme preparations or compounds for the in situ synthesis of nitrous acid).

It may also be preferred in certain embodiments for the kit to comprise one or more sticks provided with a control reagent, (which typically will give rise to a known result), thereby facilitating interpretation of the test results. Preferably the control reagent will be a positive control, but if desired a negative control stick may be provided instead of, or in addition to, the positive control stick. The control sticks, if included in the kit, are clearly marked, so as to be distinguishable from the test sticks.

In a third aspect, the invention provides a method of testing for the presence of an analyte in a sample liquid supported on a test surface, comprising using a test stick having a handle portion to be held by a person performing the test and a mixing portion bearing a dried, pre-dosed reagent for the test, such that the mixing portion of the test stick is contacted with the sample liquid so as to reconstitute the test reagent, and moving the mixing portion relative to the test surface so as to cause mixing of the reconstituted reagent with the sample liquid.

The invention can be applied in a wide range of assays. By way of example only, this range includes any assay conventionally conducted using the principle of particle agglutination. Such assays are routinely used to detect infective organisms such as *H. pylori*, Neisseria, Streptococci, Legionella, *E. coli*, Salmonella and Staphylococcus. Particularly preferred are kits for performing "Lancefield grouping" of Streptococci. Other examples of assays which may be conducted in accordance with the present invention include rapid biochemical tests for oxidase, in which tetramethyl-p-phenylene diamine dihydrochloride with ascorbic acid is used for differentiating oxidase-positive organisms e.g. *Neisseria gonorhoeae*, from oxidase-negative organisms (e.g. *E. coli*); and β-lactamase tests, which utilise Nitrocefin, a chromogenic substrate, for rapid detection of penicillinase-producing strains. In most cases the reagents would be dried on a test stick in accordance with the invention, the stick being used for collecting bacterial cells by contacting colonies growing on solid media. Additional liquid such as water, saline solution or buffer solution will be required in some cases.

DETAILED DESCRIPTION OF THE INVENTION

Figure 1:
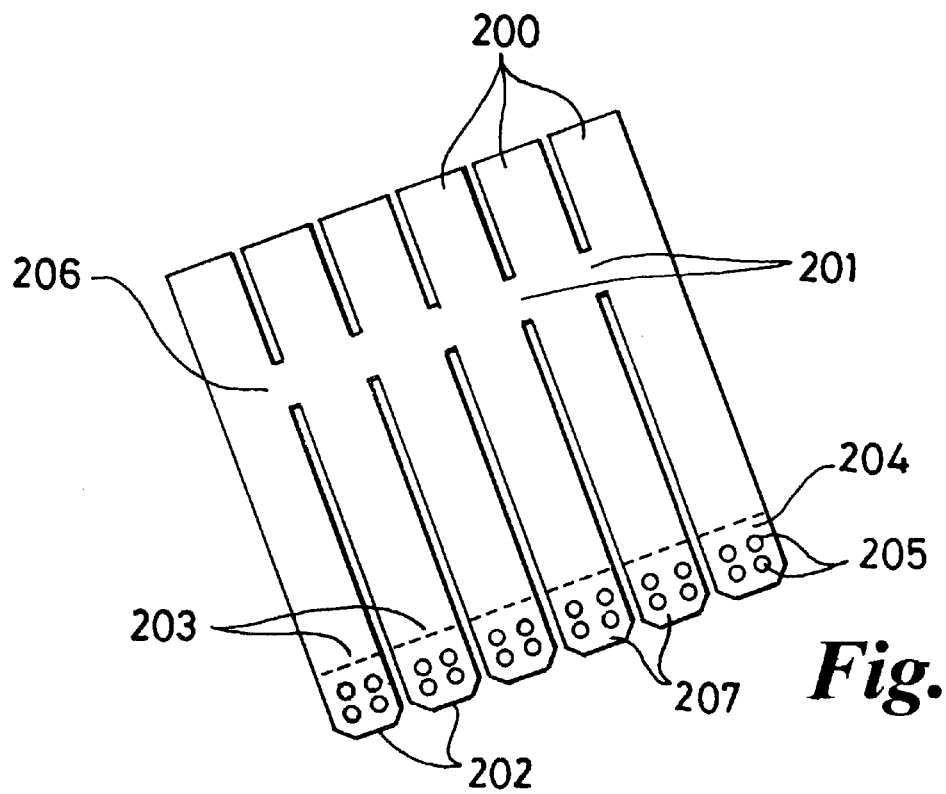
FIG. 1 shows an array of "tear-off" test stick assay devices in accordance with the invention.

Referring to FIG. 1, the test sticks 200 comprise a side-by-side arrangement of sticks which have been cut or stamped from a sheet of card. The cutting or stamping has left a small web 201 of card material joining each adjacent pair of sticks. The sticks 200 are therefore clearly distinct from one another, but are joined together in the array and readily separated by hand from one another by tearing the residual web 201. The corners of one end 202 of each stick 200 are cut off so that this has distinctive shape. The end region 207 about end 202 of each stick 200 constitutes the mixing portion which is the working end of the stick in use. A short distance up the stick 200 from end 202 is a partial transverse cut 203 across the entire width of each stick, which ensures that the mixing portion 207 of the stick is easily bent out of alignment when the stick is pressed downwards against a solid surface, such as the surface of a test card. The region 206 constitutes the handle portion of each test stick 200.

Each stick 200 is about 40 mm long and 11 mm wide. The handle portion 206 is about 30 mm long, the mixing portion about 10 mm long.

The surface 204 of the mixing portion 202 which forms the underside of the mixing portion 207 when the stick 200 is bent, bears a dried pre-dosed reagent 205. As depicted in FIG. 1 this is deposited as four closely-spaced spots of reagent.

Figure 2:
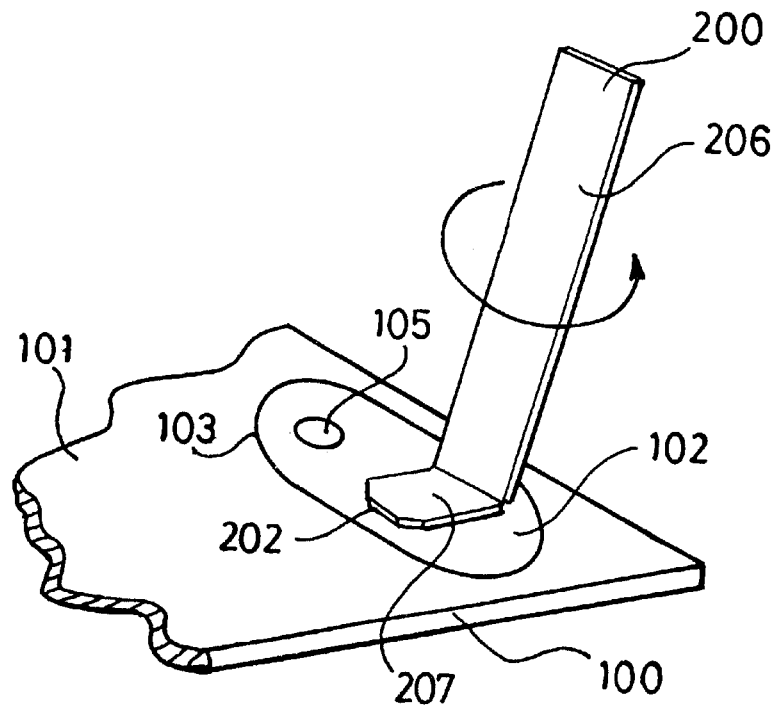
FIG. 2 shows one of the test sticks, separated from the remainder of the array, in use.

FIG. 2 shows a test stick 200 in use. The stick 200 is in contact with a test card surface 101 and the stick mixing portion 207 is bent out of alignment with the handle portion 206 thereof. The stick 200 is being used in a scrubbing or stirring motion to move sample material and reagents within the test area 102 defined by line 103 on the test card 101.

EXAMPLES

Example 1

The following, which is given by way of example only, illustrates the manufacture of a test kit in accordance with the invention.

A *Helicobacter pylori* Latex Agglutination Test comprises a Dry Spot™ latex reagent. The reagent consists of polystyrene latex particles of size 350 nm coated with a soluble extract of *H. pylori* cells. This is prepared in a phosphate buffer pH 7.3 which contains bovine serum albumin at a concentration of 10 mg per ml and sucrose at a concentration of 80 mg per ml. The latex particle concentration is approximately 85 mg per ml.

The reagent is deposited onto the mixing portion surface of a polypropylene-laminated card test stick in volumes of 1.25 μl (4 spots providing a total of 5 μl per test stick). This is done using a syringe pump system and an X-Y table to allow for precise positioning. The resulting stick is as seen in FIG. 1. The sticks are provided in strip-arrays of 10, partially joined to allow easy separation, as seen in FIG. 1.

The kit also includes positive and negative control sticks. Human serum, demonstrated to contain specific anti-*H. pylori* antibody (positive) or demonstrated not to contain specific anti-*H. pylori* antibody (negative), is diluted and sucrose added to provide a concentration of 80 mg per ml. The positive or negative control serum is deposited onto the mixing portions of respective positive or negative control sticks in volumes of 1.25 μl (4 spots, a total of 5 μl per stick). The sticks are clearly marked as positive or negative controls, but are otherwise substantially identical to the test sticks.

The control reagents can be reconstituted on a test surface using, for example, distilled water or aqueous buffers (such as phosphate-buffered saline), and then processed with a test stick in the usual way as if it were a normal sample liquid.

The spots of test and control reagents are dried on the card surface using a combination of warm air and infrared energy on a moving conveyor belt. The test stick arrays are packed in moisture impermeable, foil-laminate pouches.

The kit also comprises a test card, of known conventional type, upon which to perform the assay.

Example 2

Lancefield Streptococcal Grouping Kit

An embodiment of the present invention provides a Streptococcus grouping kit which can be used in conjunction with nitrous acid or enzyme extraction procedures for rapid identification of β-haemolytic streptococci of Lancefield types A, B, C, D, F and G.

Differentiation between the various Lancefield groups of Streptococci may be desirable for clinical treatment and/or for epidemiological purposes.

The kit comprises six foil pouches, each containing 6 arrays of 10 test reagent sticks, substantially as shown in FIG. 1. Each of the six pouches contains sticks having test reagents specific for one of the six Lancefield group antigens A, B, C, D, F or G. The test reagent comprises dried, pre-dosed blue monodisperse latex particles sensitised with rabbit antibody directed against the appropriate antigen. The kit thus comprises 60 test sticks for each Lancefield group.

The it further comprises:—3 strips of 10 sticks pre-dosed with positive polyvalent control reagent (dried antigen extract from group A, B, C, D, F and G Streptococci); white disposable test cards which provide a test surface for supporting the sample liquid; a plastics clip for re-sealing the foil pouches once opened; and instructions for use. As in Example 1, the test and control reagents are provided in an array of four dried drops, each originally of 1.25 μl volume.

The kit may be produced as follows:

Specific rabbit hyperimmune anti-streptococcal antisera are produced by standard techniques. Lancefield group antisera A, B, C, D, F, and G are produced from separate groups of rabbits and minor cross reactions occurring with other bacteria are absorbed out. The antibody in the sera is partially purified by ammonium sulphate precipitation and dialysis against phosphate buffered saline pH 7.3.

Blue latex particles of diameter 300–400 nm are suspended in phosphate buffered saline to make a 1% concentration. The temperature of the particle suspension is raised to 55° C. in a water bath and the purified antibody is added. After a period of 30 minutes incubation the vessel is removed from the water bath and the latex suspension is centrifuged at 4000 rpm to sediment the particles. The sensitised latex is then re-suspended at a concentration of 10% in phosphate buffered saline containing 1% BSA and 6% sucrose.

After filtration the suspension is spotted onto cards or sticks using an automated microdosing syringe system in volumes of 5 μl per test (4×1.25 μl spots).

The spots are dried at a temperature of 60° C. and when cool the sticks are placed in a moisture impermeable foil pouch and a silica gel sachet added to remove any moisture which may enter at subsequent pouch openings.

Test Procedure

1. Using known enzymatic or acid extraction methods (Maxted 1948 Lancet (ii) 255–256, Ederer et al, 1972 Appl. Microbiol. 23, 285–288; Lancefield 1938 Proc. Soc. Exp. Biol. 38, 473–478) an antigenic extract is prepared from a fresh culture of the organism (preferably grown on a blood agar plate overnight at 37° C.). The reagents for performing the antigen extraction are included in the kit in some embodiments.

2. Using a pasteur pipette a 50 μl drop of sterile saline is added to a small circle at the base of an oval reaction area marked on the test card.

3. A positive control stick is removed from the pouch by tearing one off from the others on the strip, taking care to avoid touching the area where the dried reagents are located (if testing more than one reagent remove the appropriate number of sticks).
4. The stick is positioned so that the coloured spots of reagent are at the bottom and the stick placed on the test card with the spots touching the liquid. The sticks is then pushed down so that it bends at the hinge. The stick is moved in a circular manner for 10 seconds to rehydrate the dried antigen extract.
5. The required number of test reagent sticks are removed from the pouch by tearing them away from the others on the strip, taking care to avoid touching the area where the spots of reagent are located. The stick is positioned so that the coloured spots are at the bottom, and then placed on the card with the spots touching the freshly prepared antigen suspension. The stick is then pushed down so that it bends at the hinge and the mixing portion used to mix the antigen suspension until the dried latex reagent is fully rehydrated and homogeneous.
6. The card is gently rocked and assessed for agglutination within the 1 minute test time.

The positive control must show agglutination with the dried test reagent within 1 minute. The test result is positive for the sample when agglutination occurs with one grouping reagent, or when one grouping reagent gives a substantially stronger reaction than the other five, within one minute. A negative result is obtained if no agglutination occurs and a smooth even blue suspension remains after 1 minute. Reactions occurring after 1 minute are to be ignored.

Those skilled in the art will appreciate that kits using the test sticks of the invention may be prepared in a manner which differs from that described above without departing from the invention. For example, the following parameters may be varied without substantially affecting the performance of the invention.

Latex particle size may vary from 100 to 900 nm diameter, with alternative colours or even natural white colour. Antibodies from other species such as goat, sheep, horse etc. or monoclonal antibody may be used. Antibody may be purified by a variety of techniques such as ion-exchange chromatography, protein A affinity chromatography etc.

The sensitisation buffer may be one of a number of suitable types including borate, glycine and Tris and the pH thereof may vary between pH 6 and 8.5, and the ionic strength may vary between 0.01 and 1 molar. The sensitisation temperature may vary between 4° C. and 60° C. At high temperatures (eg. 60° C.) the reaction may reach equilibrium within 10–15 minutes, whereas at low temperatures (eg. 4° C.) it may be necessary to leave the reaction mixture for up to 18–24 hours. Further washes may be used to remove additional unbound antibody.

The BSA concentration in the resuspended particle mixture may be varied form 0.05–3% or more. The reagent concentration used for spotting may be varied between 1% and 20% solids. Spotting volumes may be varied to suit concentration and reaction visibility requirements. Drying temperatures and times can be varied to suit air flow and evaporation rate.

We claim:

1. An assay device for testing for the presence of an analyte in a sample liquid, the device comprising a test stick having a handle portion to be held by a person performing the test and a mixing portion to contact the sample liquid, the mixing portion bearing a dried, pre-dosed reagent for detecting the analyte, the dried reagent comprising an antibody specific for a Lancefield group-specific streptococcal antigen, and being reconstituted by contact of the mixing portion of the test stick with the sample liquid, and wherein the mixing portion is configured to provide a mixing surface to mix the reconstituted reagent with the sample liquid supported on a test surface not forming part of the test stick.

2. An assay device according to claim 1, wherein the dried reagent is deposited on the mixing portion as a plurality of closely-spaced spots.

3. An assay device according to claim 1, wherein the dried reagent is particulate and the test result is revealed by the occurrence of, or inhibition of, agglutination of the particles following mixing with sample liquid.

4. An assay device according to claim 1, wherein the test stick comprises a strip of card having a foldable tip.

5. An assay device according to claim 1, wherein there is provided a line of weakness between the mixing and handle portions.

6. An assay kit comprising a plurality of assay devices in accordance with claim 1, each assay kit having instructions for use, and each of the assay devices comprising a said test stick.

7. An assay kit according to claim 6, comprising a plurality of disposable test sticks in the form of a perforated array of individually detachable card strips.

8. An assay kit according to claim 6, further comprising one or more components selected from the group consisting of: test sticks bearing a dried, pre-dosed positive or negative control reagent; reagents for preparing an extract of Lancefield group-specific antigen from Streptococci; and a test card providing a test surface for supporting the sample liquid during the assay.

9. A method of testing for the presence of an analyte in a sample liquid, comprising using a test stick having a handle portion to be held by a person performing the test and a mixing portion bearing a dried, pre-dosed reagent for the test which reagent comprises an antibody specific for a Lancefield group-specific streptococcal antigen; contacting the mixing portion of the test stick with the sample liquid supported on a test surface not forming part of the test stick so as to reconstitute the test reagent; moving the mixing portion relative to the test surface so as to cause mixing of the reconstituted reagent with the sample liquid; and determining the test result.

* * * * *